(12) United States Patent
LaSala (10) Patent No.: US 6,726,635 B1
(45) Date of Patent: Apr. 27, 2004

(54) CARDIAC IMPULSE DETECTOR

(76) Inventor: Anthony F. LaSala, 926 N. Main St., West Hartford, CT (US) 06117

( * ) Notice: Subject to any disclaimer, the term of this patent is extended or adjusted under 35 U.S.C. 154(b) by 0 days.

(21) Appl. No.: 09/570,695

(22) Filed: May 12, 2000

(51) Int. Cl.$^7$ .................................................. A61B 7/04
(52) U.S. Cl. ........................... 600/528; 381/67; 181/131
(58) Field of Search ............................... 600/508, 509, 600/513, 514, 515, 527, 528, 586; 181/126, 130, 131, 134, 135; 381/67; D24/134

(56) References Cited

U.S. PATENT DOCUMENTS

| | | | |
|---|---|---|---|
| 3,290,521 A | 12/1966 | Coleman et al. ............... 607/28 |
| 3,908,639 A | 9/1975 | McIntyre ................. 128/2.05 R |
| 4,362,164 A * | 12/1982 | Little et al. ................... 128/639 |
| 4,945,916 A * | 8/1990 | Kretschmer et al. ......... 128/671 |
| 5,003,605 A * | 3/1991 | Phillipps et al. ............... 381/67 |
| 5,010,889 A | 4/1991 | Bredesen et al. ............. 128/715 |
| 5,140,991 A | 8/1992 | Niwa .......................... 128/687 |
| 5,178,151 A | 1/1993 | Sackner ....................... 128/672 |
| 5,218,969 A | 6/1993 | Bredesen et al. ............ 128/710 |
| 5,467,771 A | 11/1995 | Narimatsu et al. ........... 128/672 |
| 5,476,486 A | 12/1995 | Lu et al. ......................... 607/28 |
| 5,497,778 A | 3/1996 | Hon .............................. 128/672 |
| 5,935,081 A | 8/1999 | Kadhiresan .................. 600/513 |
| 6,005,951 A * | 12/1999 | Grasfield et al. .............. 381/67 |
| 6,053,872 A * | 4/2000 | Mohler ......................... 600/485 |
| 6,324,289 B2 * | 11/2001 | Orten ............................ 381/67 |
| 6,415,033 B1 * | 7/2002 | Halleck et al. ................ 381/67 |

* cited by examiner

Primary Examiner—Jeffrey R. Jastrzab
Assistant Examiner—Frances P. Oropeza
(74) Attorney, Agent, or Firm—McCarter & English LLP (57) ABSTRACT

An apparatus and method for detecting infrasonic cardiac apical impulses of a patient including a sensor disposable in contact with skin of the patient for producing a signal responsive to a motion of the skin at an infrasonic cardiac apical impulse point of the patient. A first circuit coupled to the first sensor for generating at least one audible output in response to the first signal and indicative of the infrasonic cardiac apical impulse. A dampening ring surrounding the sensor for dampening the relative motion of the sensor with respect to movement of the patient.

29 Claims, 8 Drawing Sheets

CARDIAC IMPULSE DETECTOR

FIELD OF THE INVENTION

The present invention relates to medical diagnostic instruments, and more particularly, to such instruments for detecting abnormal heart functions.

BACKGROUND INFORMATION

Patients occasionally develop heart disease, the prompt and timely discovery of which can be determinative of patients' health and survival. Until the 19th century, medical caregivers had to press their ears against patients' chests in order to hear heart sounds. When the stethoscope ("spy of the chest" in Greek) was introduced by René Laennec (1781–1826), it enabled medical caregivers to hear heart sounds with improved ease and clarity. "In search of the perfect stethoscope that hears all heart sounds, and explains them to you." (Laennec)

The ballistic recoiling of the heart produces a vibration when it moves its apex upward, rightward, and against the underside of the chest wall before the ejection of blood. This motion or vibration is typically inaudible and infrasonic, having a sound frequency of less than about 30 Hertz. There are other low frequency, low amplitude vibrations which normally occur during cardiac filling. There are also abnormal cardiac vibrations with sound frequencies as low as about 10 Hertz, but of high amplitude that occur when the heart fills abnormally. The period of cardiac filling is called diastole, and when these abnormal vibrations occur, they indicate diastolic dysfunction of the heart. These abnormal vibrations during diastole are called pathologic gallops. Some gallops are faint and difficult to hear, and some are infrasonic.

There are two types of pathologic gallops of primary clinical significance: An S4 type of gallop, which occurs during late diastole; and an S3 type of gallop, which occurs during early diastole. Many gallops are palpable and visible even when they are inaudible. This is because they are of high-energy amplitude despite their low frequencies. Detection of gallops is very important, and can lead to the diagnosis and treatment of such cardiac disorders as hypertrophic heart syndromes, valvular lesions, cardiomyopathies, and congenital heart problems.

A visual and palpable assessment of cardiac motion of a patient in the supine position may be made at the left chest wall near the left breast. This location is called the cardiac apical impulse, and for purposes of clarity is also herein referred to as the cardiac apical impulse point. The cardiac apical impulse point is a single area typically less than about 15 millimeters in diameter. The skin motion at this location is normally caused by the recoiling of the heart when it moves its ventricular apex upward, rightward, and against the underside of the chest wall. Presently, medical caregivers may examine the heart motions at the cardiac apical impulse point by placing their fingertips against the skin at this point to enable tactile detection of apical impulses having sufficient amplitude.

Over the past 60 years, sophisticated and elaborate laboratory apparatus have been developed to detect and record heart movements, and enable medical caregivers to analyze the data for indications of abnormal heart conditions. The apexcardiogram ("ACG"), for example, which was in popular use until the early 1980's, was capable of revealing low frequency heart motions by means of electromechanical sensors affixed to a patient's chest. The ACG signals were recorded on a strip chart recorder for later analysis. An electrocardiogram ("EKG") and a separate phonocardiogram were required to be performed contemporaneous with the ACG in order to provide correlation between the low frequency heart motions and the additional heart signals. The three charts were then correlated, as by technicians, for later analysis by caregivers. Although this method was very useful for detecting heart irregularities in suspected cases, the time delay incurred by a patient between seeing a physician for referral to an ACG laboratory, testing in the laboratory by technicians, correlation of strip chart results, and analysis and diagnosis by at least one physician, generally hindered prompt and effective treatment in time-critical cases. In addition, the large expense for this labor-intensive procedure may have precluded its use in many instances.

By the mid-1980's, the ACG had been generally displaced by the echocardiogram. The echocardiogram uses ultrasonic waves to monitor heart function and provides more detail than the ACG. Unfortunately, the echocardiogram suffers from some of the same drawbacks as the ACG, including the requirement for special laboratory testing and associated expense. Like the ACG, the echocardiogram also fails to produce recognizable sounds indicative of the infrasonic heart motions, and therefore fails to disclose a method for their discovery.

Various other prior art systems are also directed toward monitoring human heart function. For example, U.S. Pat. No. 5,218,969 to Bredesen et al. ("the '969 patent") depicts an electronically enhanced stethoscope for detecting heart sounds. However, the '969 patent teaches filtering out sounds below 50 Hz (see FIG. 3F). Since human hearing is generally recognized to extend to at least as low as 30 Hz, the stethoscope of the '969 patent is not capable of detecting heart vibrations of frequency below the range of human hearing, even if it may amplify low amplitude sounds which are above 50 Hz. Accordingly, the electronic stethoscope of the '969 patent does not detect infrasonic cardiac apical impulses, and in fact is incapable of detecting any phenomena emitting a frequency below 50 Hz.

U.S. Pat. No. 5,178,151 to Sackner ("the '151 patent") shows another system for detection of heart irregularities. The '151 patent shows placement of a plurality of motion transducers about the thoracic region of a patient's chest wall. Blood vessel volume, blood pressure waveforms, and other thoracic motions including respiratory and cardiac apical motions are measured as conglomerate signals that must be further analyzed to determine the presence of heart irregularities. Due in part to its bulk, complexity, cost, and requirement for further analysis, this system suffers from design constraints that generally preclude its inclusion in a general caregiver's office. The apparatus of the '151 patent further lacks provision for transmitting the acoustic heart waveform data typically relied on during a routine physical examination.

The basic acoustic stethoscope, whether electronically amplified, filtered or not, can only be used to hear what Rene Laennec heard with his original wooden device. Only a small percentage of the vibrations of the heart are actually detected by an acoustic stethoscope. These audible vibrations range between about 40 Hertz to 500 Hertz and about 0.002 to 0.5 dynes/cm$^2$ (amplitude). The remaining vibrations are inaudible because of the typical thresholds of human hearing. Infrasonic vibrations of sufficient amplitude have heretofore only been detectable with bulky, complex, and costly apparatus requiring labor intensive analysis. Heart gallops rest near the division of audible and infrasonic vibrations. Heart gallops have been called the heart's "cries for help." Detection of these vibrations is important in diagnosing cardiac pathology and is why palpation of the cardiac apical impulse is an extremely important, yet often neglected, part of the cardiac exam.

All in all, the above-described prior art fails to recognize the utility of detecting infrasonic heart motions and producing audible outputs that are indicative of those motions. Such prior art also fails to put infrasonic heart motion data in context with traditional acoustic heart data. It is therefore an object of the present invention to overcome the above-described significant drawbacks and disadvantages of the prior art.

SUMMARY OF THE INVENTION

The present invention is directed to a cardiac impulse detector for use in routine cardiac examinations, which employs a sensor capable of detecting infrasonic cardiac apical impulses of a patient. The detector produces audible and optionally visual outputs indicative of those impulses for contemporaneous consideration by a medical caregiver when the sensor is placed in contact with the patient's skin surface at the cardiac apical impulse point.

In an embodiment of the present invention, a sensing protrusion or button is placed in contact with the skin surface of the patient at the patient's cardiac apical impulse point. The cardiac apical impulse point is located near the left breast. The sensing button is mounted to a piezoelectric sensor, and causes the sensor to respond to the infrasonic heart motions or impulses at the cardiac apical impulse point of the patient. A circuit is electronically connected to the piezoelectric sensor and generates audible and visual outputs indicative of the heart motions. The piezoelectric sensor is housed in one end of an hourglass shaped housing, which provides the caregiver with a convenient grip for holding the device against the cardiac apical impulse point.

This embodiment of the detector further employs a traditional acoustic diaphragm mounted at the opposite end of the housing relative to the piezoelectric sensor. The acoustic diaphragm can transmit acoustic heart sounds to an earpiece worn by the caregiver when the acoustic end of the sensor housing is placed in contact with the patient's chest, and a selection manifold has been rotated 180 degrees in order to transmit the traditional acoustic sounds instead of the signals indicative of infrasonic heart motions. The sounds may be electronically amplified and/or filtered. This embodiment has the distinct advantage of placing the audible signal indicative of an infrasonic cardiac impulse in temporal context with the traditional acoustic cardiac sounds familiar to the caregiver.

In accordance with another aspect of the present invention, an apparatus is provided for detecting infrasonic cardiac apical impulses of a patient. The apparatus comprises a flexible substrate including (i) a skin-contacting surface located on one side of the substrate that is disposable in contact with a skin surface region of a patient defining an infrasonic cardiac apical impulse point, and is movable with the contacted skin surface region in response to a subaudible motion of the contacted skin at the infrasonic cardiac apical impulse point; and (ii) a reflective surface located on an opposite side of the substrate relative to the skin-contacting surface and movable with the skin-contacting surface in response to a subaudible motion of the contacted skin at the infrasonic cardiac apical impulse point. A light source, such as a laser, is spaced apart from and faces the reflective surface of the substrate. The light source transmits light onto the reflective surface, and the reflective surface reflects light transmitted thereon by the light source. An optical sensor is spaced apart from and faces the reflective surface. The optical sensor receives reflected light directed by the reflective surface and generates a first signal indicative of movement of the reflective and skin-contacting surfaces and corresponding to a subaudible motion of the contacted skin at the infrasonic cardiac apical impulse point. An electric circuit is coupled to the optical sensor for generating (i) an audible output and/or (ii) a visual output, in response to the first signal and indicative of an infrasonic cardiac apical impulse.

In accordance with another aspect, the present invention is directed to a method for detecting infrasonic cardiac apical impulses of a patient, comprising the following steps:

(i) providing a flexible substrate including a skin-contacting surface located on one side of the substrate and a reflective surface located on an opposite side of the flexible substrate relative to the skin-contacting surface;

(ii) positioning the skin-contacting surface of the flexible substrate in contact with a skin surface region of the patient defining an infrasonic cardiac apical impulse point on the patient's chest;

(iii) allowing movement of the skin-contacting and reflective surfaces of the flexible substrate with movement of the skin surface region of the patient in response to a subaudible motion of the skin at the infrasonic cardiac apical impulse point;

(iv) transmitting light from a light source onto the reflective surface of the flexible substrate positioned on the skin surface region of the patient defining the infrasonic cardiac apical impulse point;

(v) reflecting transmitted light from the light source with the reflective surface of the flexible substrate positioned on the skin surface region of the patient defining the infrasonic cardiac apical impulse point;

(vi) receiving with an optical sensor reflected light directed by the reflective surface, and generating a first signal indicative of movement of the reflective and skin-contacting surfaces and corresponding to a subaudible motion of the skin at the infrasonic cardiac apical impulse point;

(vii) processing the first signal electronically; and (viii) generating (i) an audible output and/or (ii) a visual output, indicative of an infrasonic cardiac apical impulse.

A primary advantage of the present invention is that it may provide an efficient way to screen patients for abnormal infrasonic vibrations or pathological gallops during routine physical examinations, a clearly desirable improvement over current procedure which requires elaborate set-up of bulky apparatus. Other objects and advantages of the present invention will become apparent in view of the following Detailed Description of the Preferred Embodiments and accompanying drawings.

DETAILED DESCRIPTION OF THE PREFERRED EMBODIMENTS

Figure 1:
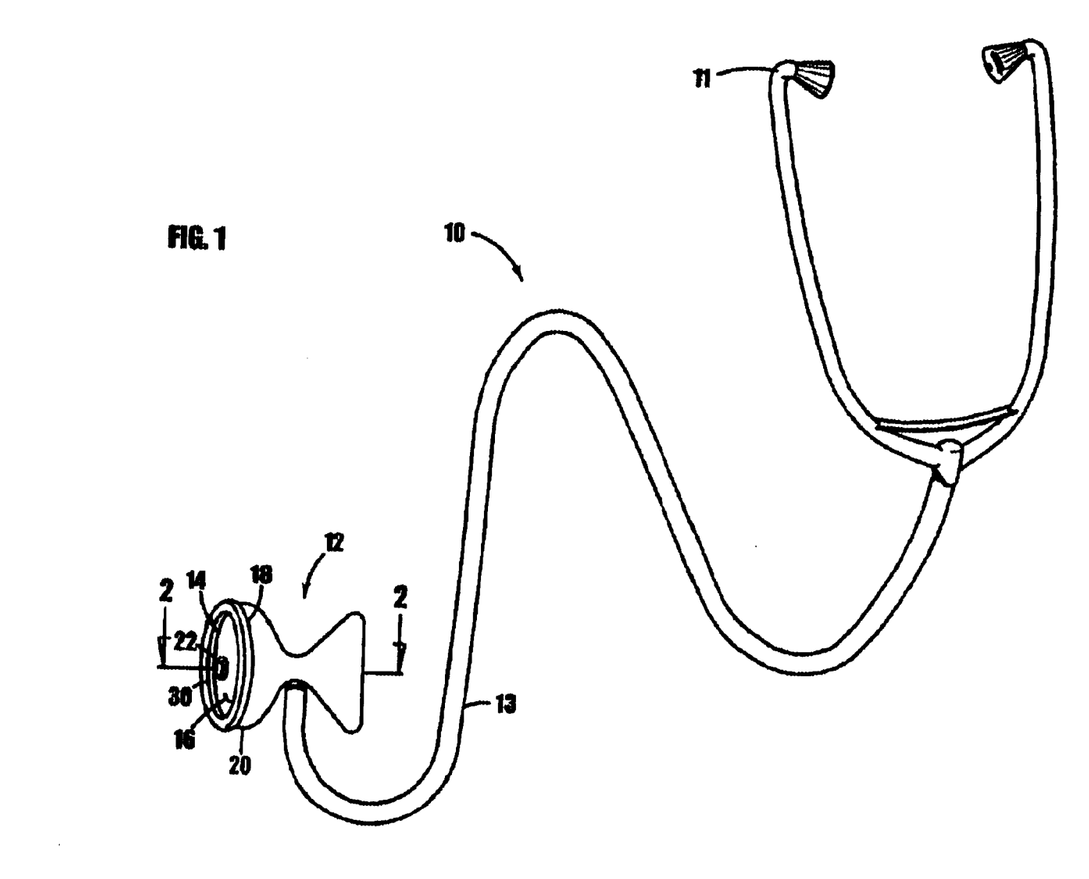
FIG. 1 is a somewhat schematic, elevational view of a first embodiment of a cardiac impulse detector embodying the present invention.

In FIG. 1, a first embodiment of the cardiac impulse detector of the present invention is indicated generally by the reference numeral 10. The cardiac impulse detector 10 comprises an earpiece 11 connected to a sensor assembly 12 via acoustic tubing 13. The sensor assembly 12 comprises a diaphragm 14 including a piezoelectric element16 superimposed over a substrate 18, wherein the diaphragm is mounted around its circumference to a housing 20. A sensing protuberance 22 is mounted to the piezoelectric element 16. A dampening member 30 is mounted to the housing 20 at one end, and surrounds the sensing protuberance 22 without contact. The housing 20 is hourglass shaped in order to transmit acoustic pressure waves with minimal attenuation and distortion, and to provide a convenient grip for placement of a caregiver's hand.

Figure 2:
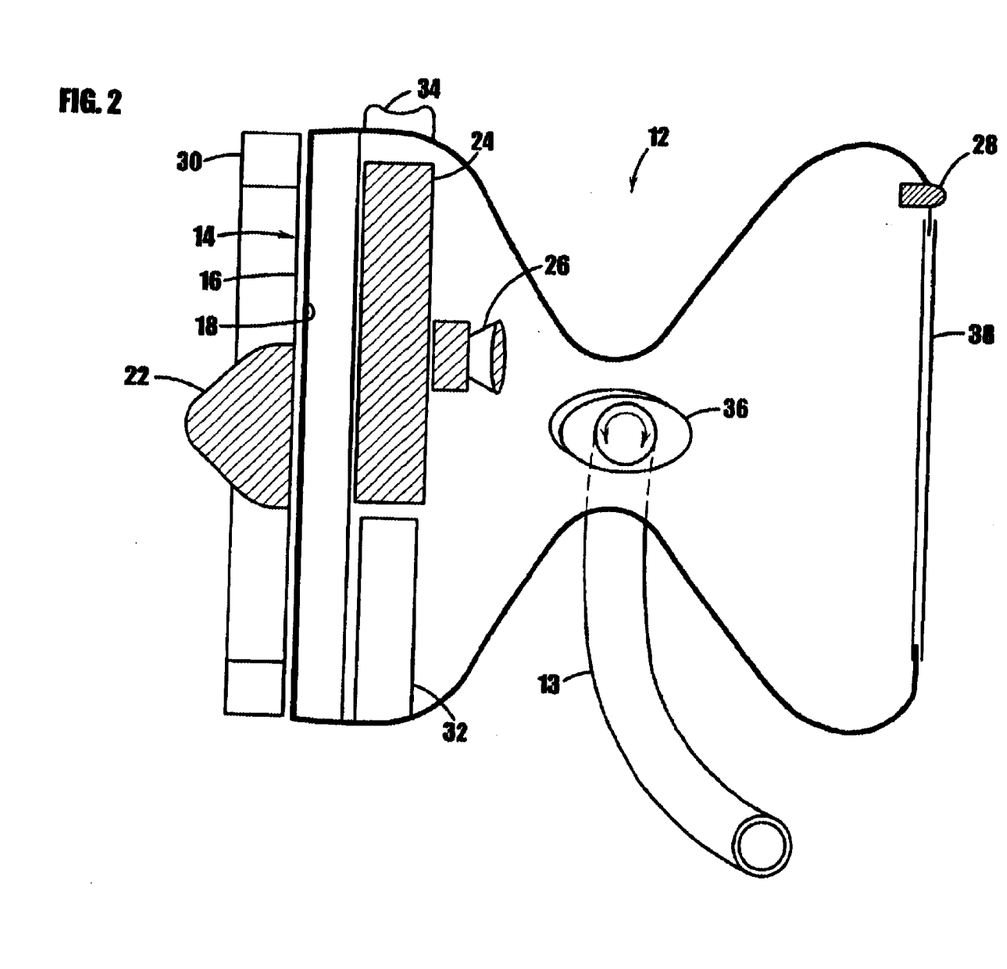
FIG. 2 is a cross-sectional view of the cardiac impulse detector taken along line 2—2 of FIG. 1.
Figure 3:
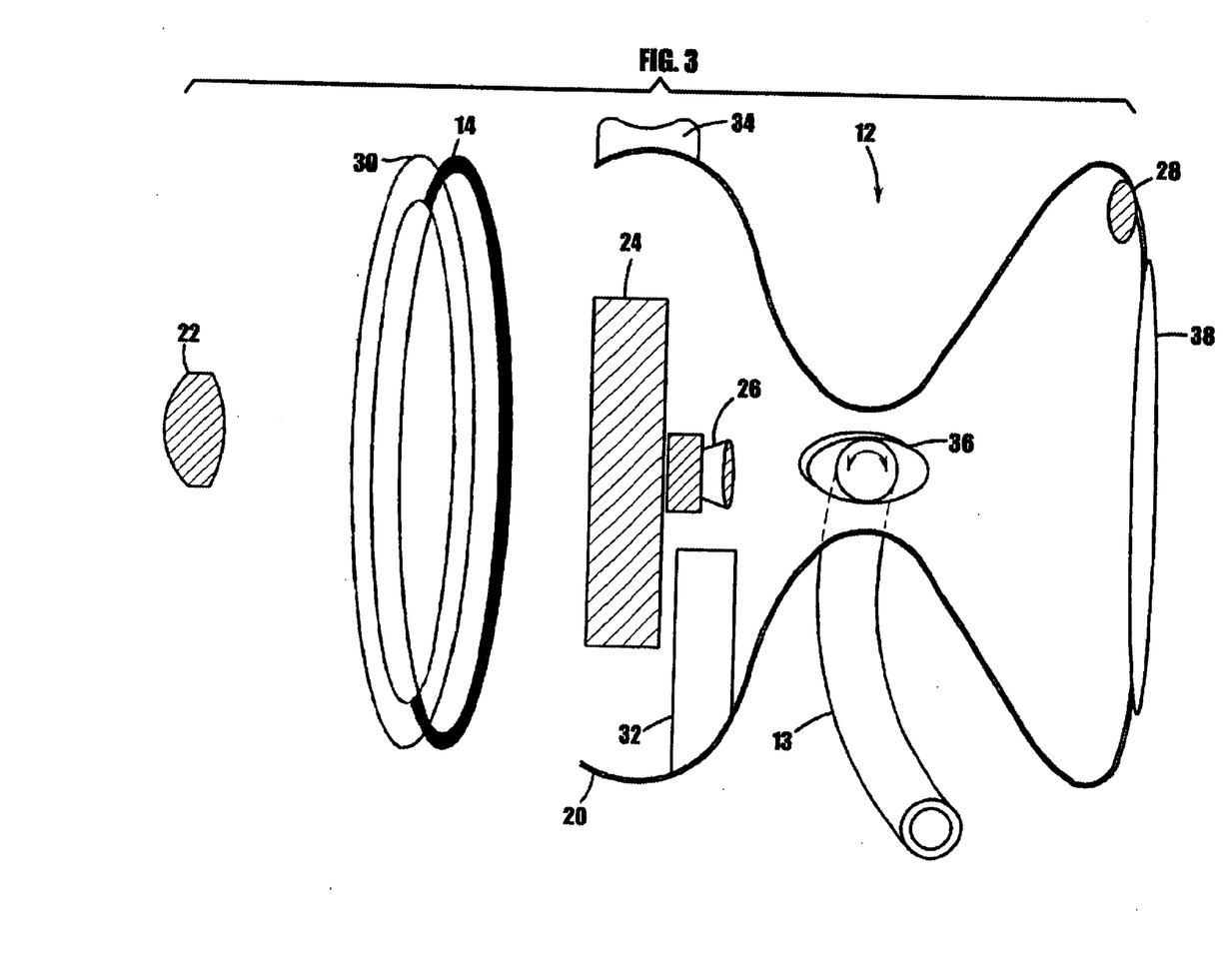
FIG. 3 is an exploded, partial, somewhat schematic, cross-sectional view of the cardiac impulse detector of FIGS. 1 and 2.

Turning to FIGS. 2 and 3, the sensing protuberance 22 is mounted to the piezoelectric element 16 at about its center. In this embodiment of the present invention, the sensing protuberance 22 is made of nylon and is rounded and convex, allowing it to nest longitudinally in the intercostal space at a patient's cardiac apical impulse point, thus coming into contact with the skin tissue over the cardiac apex. As the ventricular apex of the heart strikes the internal surface of the rib cage, it generates an impulse, which, coupled through the tissue, strikes the sensing protuberance 22. As may be recognized by those skilled in the pertinent art based on the teachings herein, the sensing protuberance 22 may take any of numerous different shapes for performing the functions of the exemplary protuberance, such as a globular, ovate, or other substantially smooth shape. Likewise, the sensing protuberance 22 may be made of any of numerous different materials for performing the functions of the protuberance described herein, such as polyurethane or thermoplastic rubber.

When the sensing protuberance 22 is struck, it deflects the diaphragm 14, and thus the piezoelectric element 16. The piezoelectric element 16 is a natural mechanical differentiator and a transducer of mechanical movement into electrical signals. When deflected, it generates a momentary charge. It is not a sustained voltage potential but a voltage spike that decays rapidly, indicating proportional changes in forces applied to the diaphragm 14. This characteristic is advantageous for this application in order to detect low frequency or infrasonic cardiac movements. When the cardiac apex strikes the sensing protuberance 22, the momentary charge is generated by the piezoelectric element 16. An electronic circuit 24 is connected to the piezoelectric element 16, and electronically detects the momentary charge indicative of the heart motion at the cardiac apical impulse point. An audio speaker 26 and a light emitting diode ("LED") 28 are connected to the electronic circuit 24, and generate outputs corresponding to the detected cardiac apical motion. These indications provide the caregiver the means to audibly and visibly observe and correlate normal and abnormal infrasonic cardiac apical impulses. As may be recognized by those skilled in the pertinent art based on the teachings herein, the speaker 26 may be supplemented or replaced by any of numerous different audible transducers for performing the functions of the speaker described herein, such as a piezoelectric buzzer, or other audible indicator. Likewise, the LED 28 may be supplemented or replaced by any of numerous different visible indicators for performing the functions of the LED described herein, such as an electrical light bulb, liquid crystal display, graphical monitor or computational device.

The diaphragm's substrate 18 is made of MYLAR® film, mounted at its outer diameter to the housing 20. As may be recognized by those skilled in the pertinent art based on the teachings herein, the MYLAR® film may be replaced with any of a number of suitable materials for performing the functions of the substrate described herein, such as spring steel or other resilient material. The diaphragm 14 is preferably taut so that it is mechanically biased, which will, in turn, lead to enhanced sensitivity when the protuberance 22 is placed on a patient.

The location of the dampening member 30 around the outer diameter of the diaphragm 14 provides a mechanical stabilizing and decoupling effect when the cardiac impulse detector 10 is placed on a patient's skin. In this embodiment, the dampening member 30 is in the form of a ring and made of foam rubber. As may be recognized by those skilled in the pertinent art based on the teachings herein, the dampening member 30 may comprise any of numerous different materials or mechanisms which now or later become known for performing the functions of the dampening member described herein, such as foam, rubber, soft polyurethane, or a hydraulic fluid damper. As also may be recognized by those skilled in the pertinent art based on the teachings herein, the dampening member 30 may take any of numerous different shapes for performing the functions of the dampening member described herein, such as oval, elongated, or rectangular. This configuration for interfacing the diaphragm 14 to the cardiac apex promotes improved signal acquisition and reduced secondary motion from the caregiver's hand or inadvertent patient movements.

The cardiac impulse detector 10 further comprises a battery 32 mounted to the housing 20, and electrically connected to a momentary power switch 34, which, in turn, is electrically connected to the electronic circuit 24 to supply power for the circuit and for the indicators 26 and 28. The battery 32 is to be replaced if the indicators do not activate when the sensing protuberance 22 is intentionally touched. In this embodiment of the present invention, the detector 10 is only active when the momentary power switch 34 is depressed, typically by operation of a caregiver's finger, which is intended to be done while the detector 10 is in place on a patient. When the finger moves from the switch 34, the power goes off, conserving energy in the battery 32.

The cardiac impulse detector 10 further comprises a traditional acoustic diaphragm 38 mounted to the opposite side of the housing 20 relative to the diaphragm 14. In operation, the sensor housing 20 is preferably placed on a patient's chest with the acoustic diaphragm 38 in unobstructed contact with the patient's chest in order to obtain the least amount of acoustic attenuation. The acoustic diaphragm responds to local sound-pressure waves in the tissue medium against its outer surface by reproducing the sound-pressure waves in the gaseous medium against its inner surface. Thereafter, the waves are propagated in substantially unattenuated form towards the closest pressure equilibrium point, normally an earpiece. The acoustic diaphragm effectively amplifies incident sounds by receiving sound pressure over a larger area than that of the equilibrium point or earpiece. As may be recognized by those skilled in the pertinent art based on the teachings herein, the traditional acoustic diaphragm 38 may be augmented or replaced with any of numerous different sensors for performing the functions of the exemplary acoustic diaphragm, such as an electronic microphone or similar device for sensing acoustic heart sounds. For example, a piezoelectric microphone may be employed to sense acoustic heart sounds, while an electronic amplifier and speaker transduce the electronic signal back into audible sound.

A selection manifold 36 is acoustically coupled to the speaker 26 and the acoustic diaphragm 38. The selection manifold enables alternate acoustic connection of the speaker 26 and the diaphragm 38. As shown in FIG. 1, the earpiece 11 is connected through the acoustic tubing 13 to the selection manifold 36 to receive sound from at least one of the speaker 26 and the acoustic diaphragm 38. A caregiver may rotate the selection manifold 36 one half turn (180°) to create a path for one sound source and block the other, thereby blocking loss of the desired sound-pressure across the unused diaphragm. The manifold 36 is turned in the opposite direction to switch between the sound sources 38 and 26.

Figure 4:
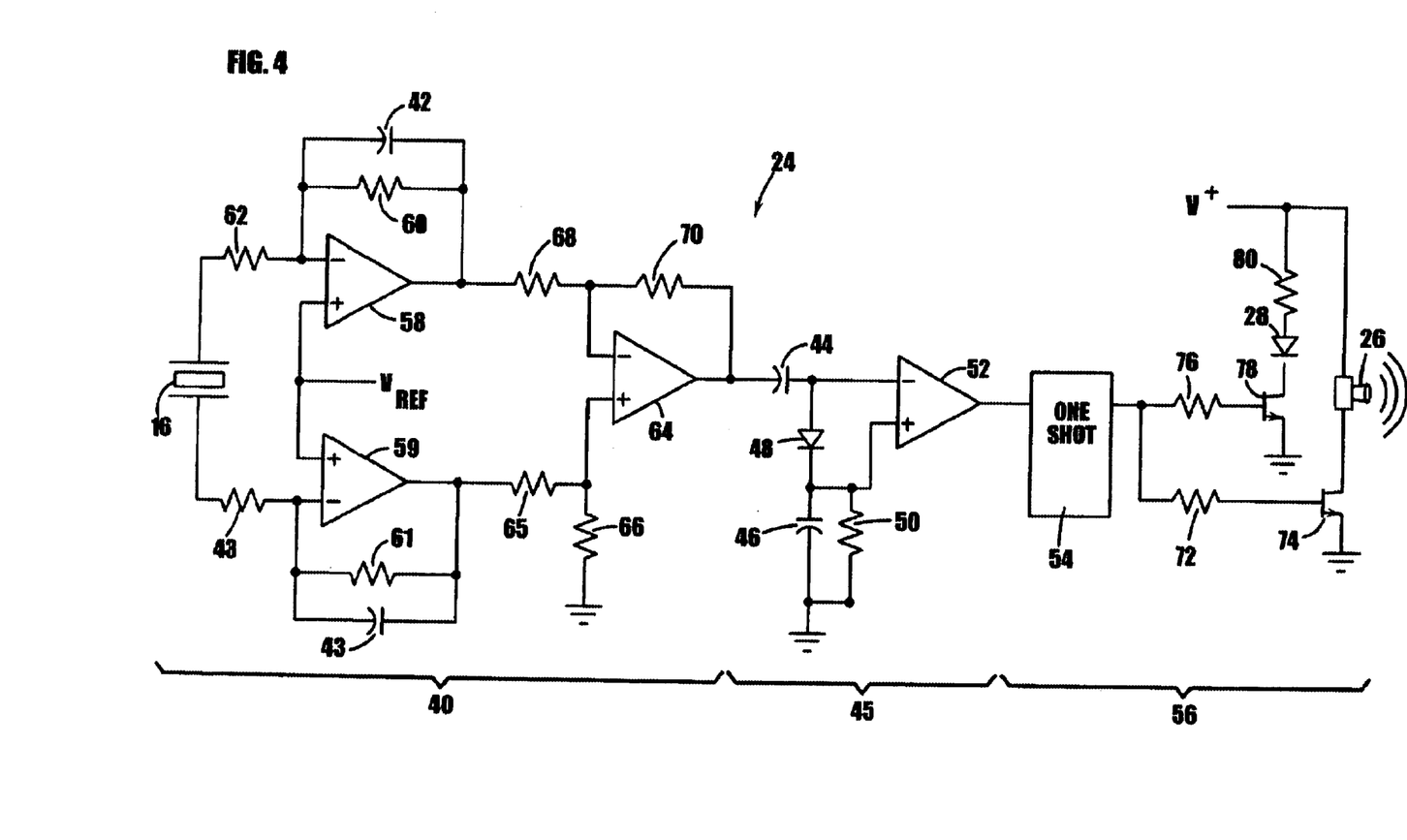
FIG. 4 is a schematic illustration of electronic circuitry of the cardiac impulse detector of FIGS. 1, 2 and 3, for driving a speaker and Light Emitting Diode in response to a sensed heart motion at the cardiac apical impulse point.

Turning now to FIG. 4, the electronic circuit 24 employs a front-end charge amplifier sub-circuit 40 of typically high gain to amplify the voltage signal generated by the piezoelectric element 16. A first differential output of the piezoelectric element 16 is connected through a resistor 62 to an inverting input of an operational amplifier ("op-amp") 58. The inverting input of the op-amp 58 is also connected to a negative feedback path comprising a capacitor 42 and a resistor 60, connected in parallel between the output of the op-amp 58 and its inverting input. The non-inverting input of the op-amp 58 is connected to a reference potential $V_{REF}$, prescribing the gain. A second differential output of the piezoelectric element 16 is connected through a resistor 63 to an inverting input of an op-amp 59. The inverting input of the op-amp 59 is also connected to a negative feedback path comprising a capacitor 43 and a resistor 61, connected in parallel between the output of the op-amp 59 and its inverting input. The non-inverting input of the op-amp 59 is connected to the reference potential $V_{REF}$, prescribing the gain. The capacitors 42 and 43 in the feedback paths enhance the amplification of the voltage potential generated by the piezoelectric element 16. A secondary amplification stage is implemented by an op-amp 64, which receives at its non-inverting input the voltage from the op-amp 59 divided across a resistor 65, with a resistor 66 completing the path to ground potential. The op-amp 64 receives at its inverting input the sum of the output of the op-amp 58 received across a resistor 68, and the direct feedback signal received across a resistor 70.

After the amplification stage, a comparator sub-circuit 45 generates a voltage pulse of variable duration corresponding to the detected cardiac apical impulse. The output from the op-amp 64 is connected across a capacitor 44 to the inverting input of a variable threshold comparator 52. The capacitor 44 functions as an AC coupled filter. The inverting input of the comparator 52 is also connected to the anode of a diode 48. Each cardiac apical impulse charges a threshold capacitor 46 through the diode 48. The cathode of the diode 48 is connected to the non-inverting input of the comparator 52. The capacitor 46 is connected to ground in parallel with a resistor 50, which sets a typically slow time constant. The resistor 50 drains charge from the threshold capacitor 46, tending to keep its voltage within the operating range of the comparator 52. The diode 48 creates a voltage difference between the two inputs to the comparator 52 by allowing current to pass from the inverting input towards the non-inverting input, thus incurring a typical voltage drop. The cathode of the diode 48 is connected to the parallel combination of the capacitor 46 and the resistor 50 to ground potential, as well as to the non-inverting input of the comparator 52. When the input signal from the capacitor 44 is below the voltage level of the threshold capacitor 46, which occurs between apical impulses, the output of the comparator 52 relative to ground potential is about one half of battery voltage or V+. When there is a cardiac apical impulse, the voltage level of the input signal from the capacitor 44 rises above the voltage level of threshold capacitor 46, switching the output to about negative one half of battery voltage or V−, thus creating a negative voltage pulse. The initial pulse-width or duration will be the width of the pulse generated by the piezoelectric diaphragm 16.

Typically, the pulse produced by the comparator 52 lacks sufficient duration to activate the speaker 26 or other audible indicator, or the LED 28 or other visual indicator. An output driver sub-circuit 56 utilizes a one-shot integrated circuit ("one-shot") 54 that is triggered by the pulse from comparator 52 to generate a single pulse of substantially constant duration. The duration of the generated pulse is independent of the duration of the incoming pulse from the comparator 52. The duration of the pulse generated by the one-shot 54 can be varied in order to optimize the outputs of the indicators 26 and 28, and to minimize the current required from the battery 32 of FIGS. 2 and 3. The output of the one-shot 54 is connected to a resistor 72, which, in turn, is connected to the base of an NPN BJT transistor 74. An emitter of the transistor 74 is connected to ground potential, and a collector of the transistor 74 is connected to the speaker 26, which, in turn, is connected to V+. Consequently, the transistor 74 drives the speaker 26 in response to the cardiac apical impulse sensed by the piezoelectric element 16. As may be recognized by those skilled in the pertinent art based on the teachings herein, the exemplary NPN BJT transistor 74 may be replaced with any of numerous different switching devices for performing the functions of the exemplary transistor, such as an FET or other suitable switching device for driving the speaker 26.

The output of the one-shot 54 is also connected to a resistor 76, which, in turn, is connected to the base of a transistor 78. An emitter of the transistor 78 is connected to ground potential, and a collector of the transistor 78 is connected to LED 28, which, in turn, is connected to V+ through a resistor 80. As may be recognized by those skilled in the pertinent art based on the teachings herein, the exemplary NPN BJT transistor 78 may be replaced with any of numerous different switching devices for performing the functions of the exemplary transistor, such as an FET or other suitable switching device for driving the LED 28.

The LED 28 can be seen by the caregiver as the cardiac impulse detector is held in place on a patient. The audible signal, generated by the speaker 26, is connected through the tubing 13 of FIG. 1 to the earpiece 11 and can be heard by the caregiver as the cardiac impulse detector is held in place on a patient.

In operation, the sensor assembly 12 of the cardiac impulse detector 10 is placed on the cardiac apical impulse point of a patient, with the sensing protuberance 22 contacting the patient's skin surface at the cardiac apical impulse point. A cardiac apical impulse induces motion of the sensing protuberance 22, which in turn causes motion of the piezoelectric element 16. The circuit 24 of FIG. 2 processes the signal from the piezoelectric element 16, and drives the speaker 26 and the LED 28 in response to the cardiac apical impulse. When a single gallop is present, the speaker will sound twice per heartbeat in a repeating series, and the LED will correspondingly flash twice in a repeating series. At a typical resting pulse rate of about 60 heartbeats per minute, the period between the two sounds indicative of the gallop is noticeably shorter than the period between successive heartbeats. If, on the other hand, the cardiac apical impulse is normal, then the speaker and LED will signal just once in a repeating series, at a rate equal to the pulse rate and will be timed with the upstroke of a peripheral pulse. Abnormal cardiac apical impulses will cause a repeating series of indications representative of the actual number of local peaks in the cardiac apical impulse waveform, where a single gallop waveform has two such peaks, and two gallops have three peaks. The housing 20 may be positioned adjacent to a patient's chest surface so that the acoustic diaphragm 38 picks up acoustic cardiac sounds and transmits them to the selection manifold 36. The selection manifold 36 may be rotated to selectively transmit the sound generated by at least one of the speaker 26 and the acoustic diaphragm 38 by rotation of the manifold. The earpiece 11 receives the acoustic signal transmitted by the selection manifold. As may be recognized by those skilled in the pertinent art based on the teachings herein, an electronic amplifier or similar device which is currently or later becomes known for performing the functions of an amplifier may be connected to the earpiece to enhance the quality of the sound received by the caregiver.

Figure 5:
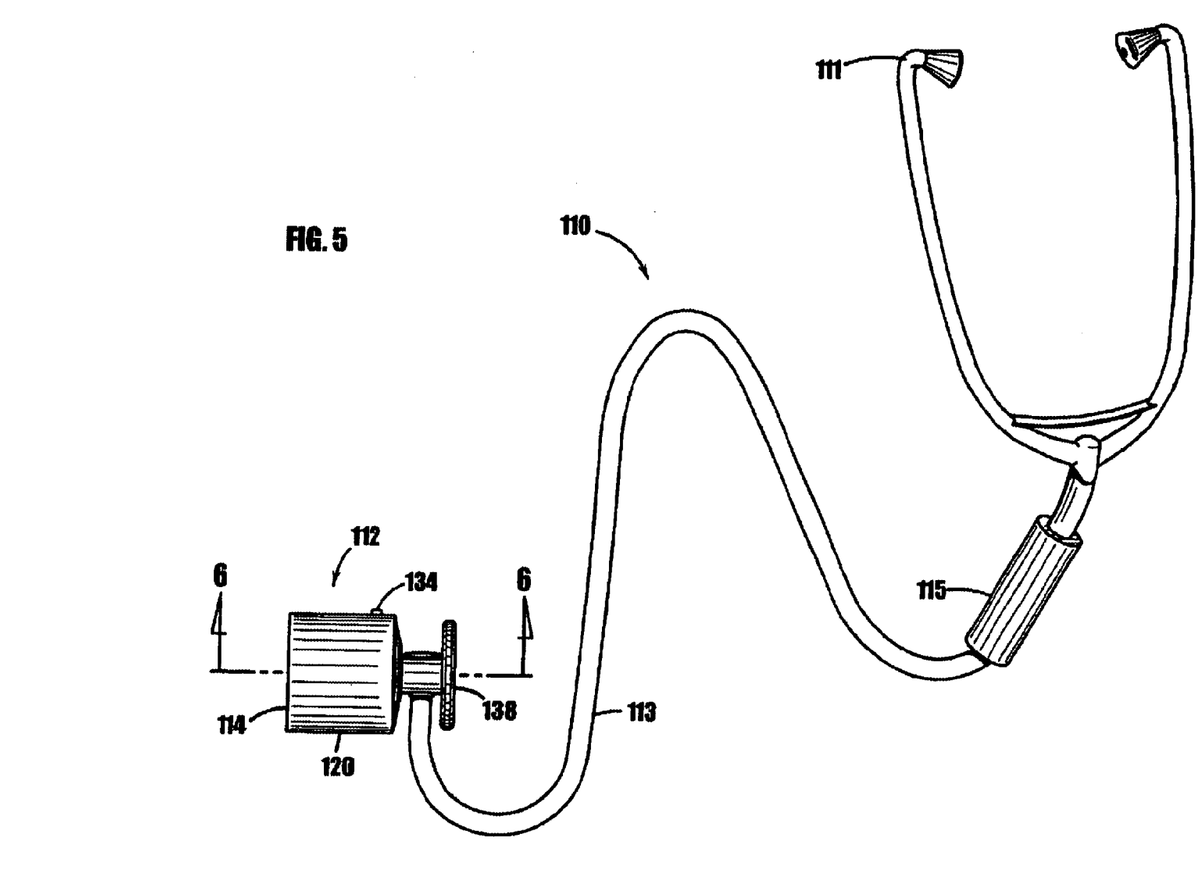
FIG. 5 is a somewhat schematic, elevational view of a second embodiment of a cardiac impulse detector embodying the present invention.
Figure 6:
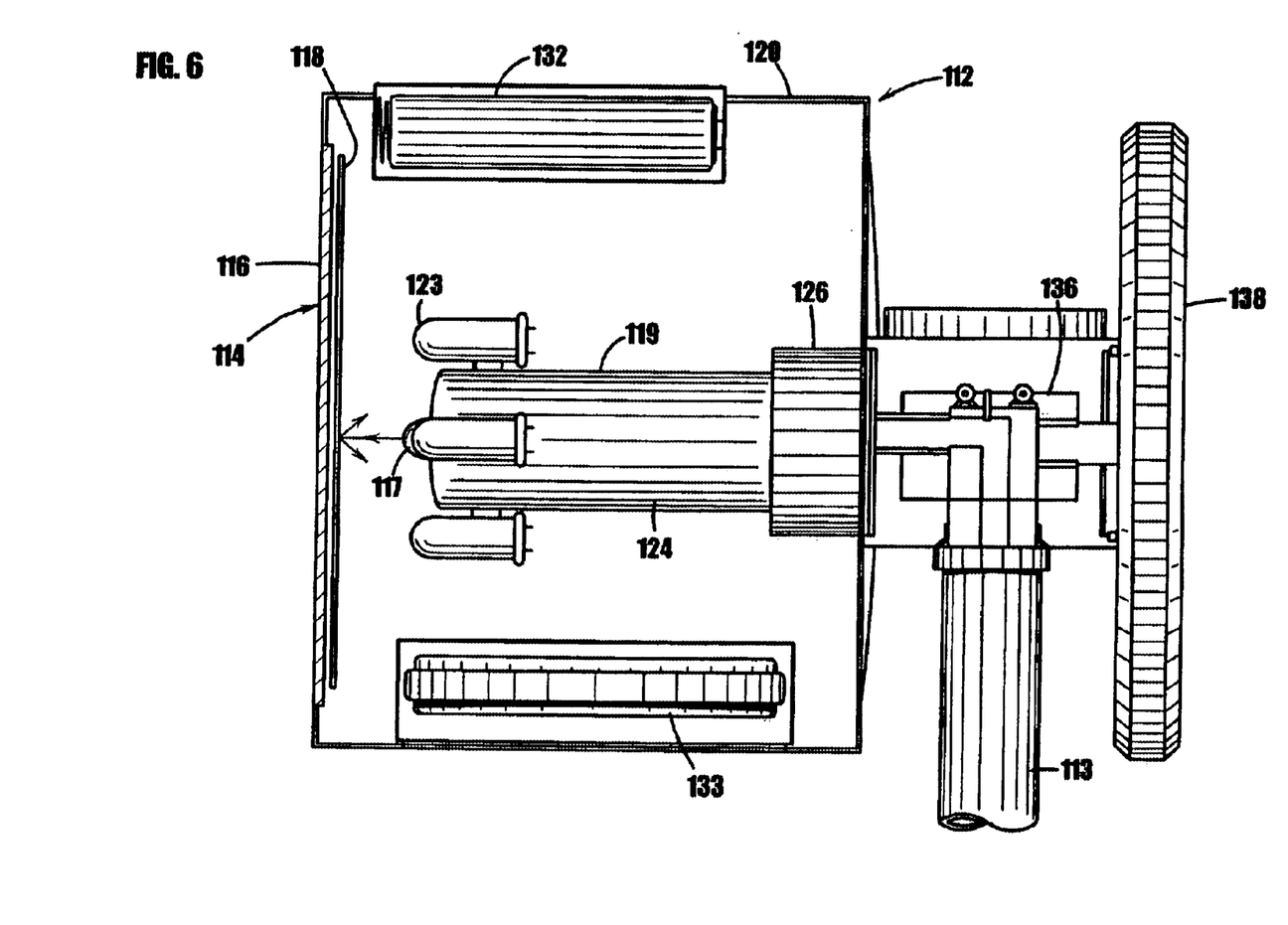
FIG. 6 is a cross-sectional view of the cardiac impulse detector taken along line 6—6 of FIG. 5.
Figure 7:
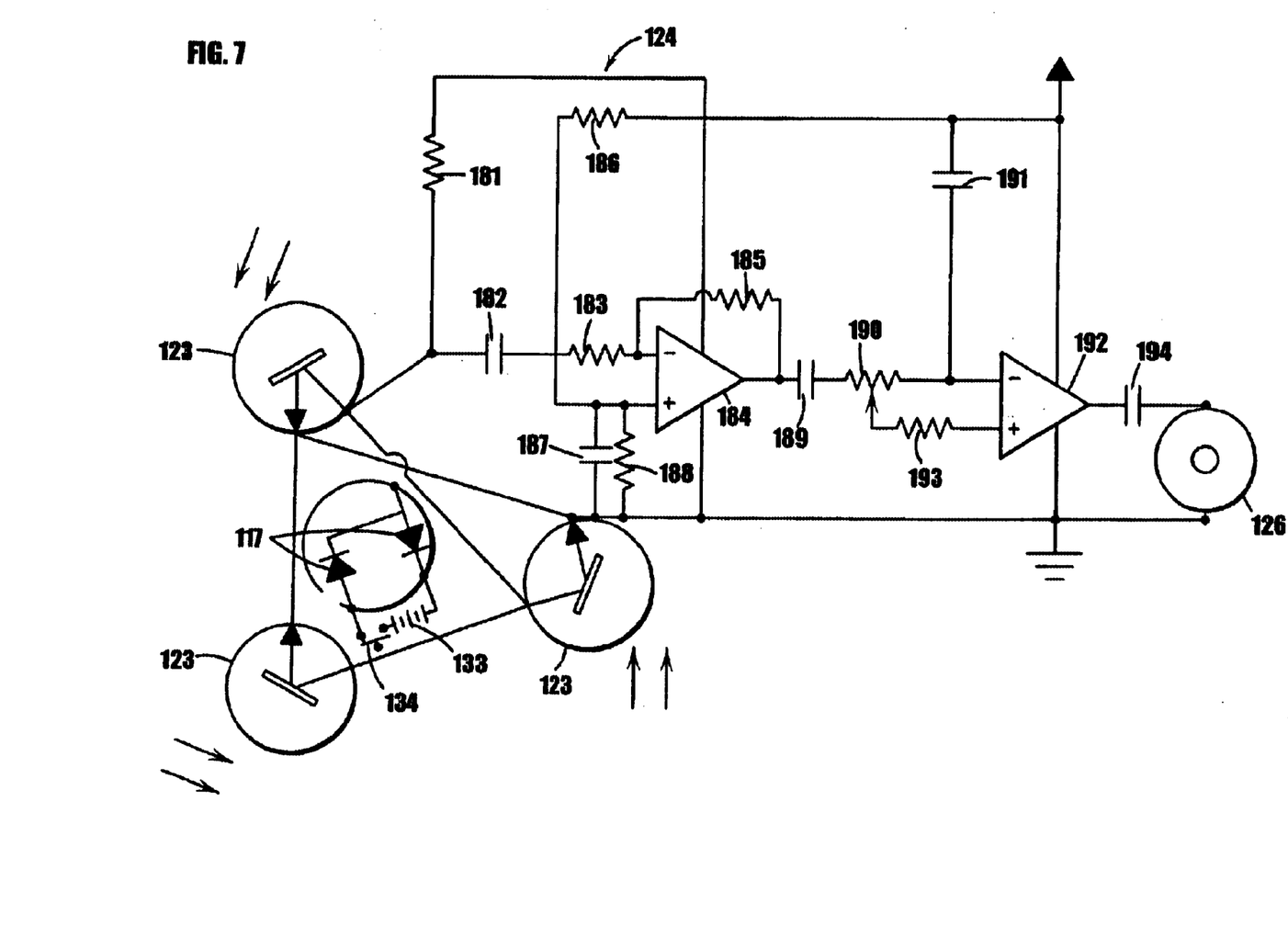
FIG. 7 is a schematic illustration of electronic circuitry of the cardiac impulse detector of FIGS. 5 and 6, for driving a speaker in response to a sensed heart motion at the cardiac apical impulse point.

In FIGS. 5 through 7, a second embodiment of the cardiac impulse detector of the present invention is indicated generally by the reference numeral 110. The cardiac impulse detector 110 is substantially similar to the cardiac impulse detector 10 described above, and therefore like reference numerals preceded by the numeral 1 are used to indicate like elements. The cardiac impulse detector 110 of FIG. 5 differs from that of FIG. 1 primarily in that the sensor assembly 112 utilizes a laser diode and compatible sensing scheme in lieu of the piezoelectric sensing scheme of the sensor assembly 12. The application and overall operation of the cardiac impulse detector 110 is substantially similar to that of the cardiac impulse detector 10. As shown in FIG. 5, the cardiac impulse detector 110 comprises an earpiece 111 connected to a sensor assembly 112 via acoustic tubing 113. The sensor assembly 112 comprises a flexible diaphragm 114 mounted about its circumference to a housing 120. An electrical power switch 134 is mounted to the housing 120 for activating the cardiac impulse detector. An audio amplifier 115 is connected to the tubing 113, and is electrically connected to the power switch 134, for enhancing the quality of the audio signal.

Turning to FIG. 6, the diaphragm 114 comprises a resilient layer 116 and a reflective layer or structure 118 superimposed over the resilient layer. In this embodiment of the present invention, the reflective layer 118 is made of any reflective material sold under the trademark REFLEXITE®. As may be recognized by those skilled in the pertinent art based on the teachings herein, the reflective layer 118 may be made of various other materials having comparably high coefficients of reflectivity, which are currently or later become known for performing the functions of the exemplary reflective layer or structure. A laser diode support 119 is mounted to an inner surface of the housing 120, and projects outwardly towards the diaphragm. A laser diode 117 is mounted to the free end of the support 119, and emits a beam of laser light towards the center of the reflective layer 118. A battery 133 is mounted to the housing 120, and is electrically connected to the laser diode 117 via a power switch 134 (FIG. 7) for supplying power to the diode. As may be recognized by those skilled in the pertinent art based on the teachings herein, the power switch 134 may comprise a single-position double-throw (SPDT) switch for fulfilling the function of the power switch 134. Phototransistors 123 are mounted to the laser support 119. The phototransistors 123 receive the reflected laser light directed by the reflective layer 118, and generate outputs indicative of the instantaneous position of the diaphragm 114 that are proportional to the infrasonic movements of the cardiac apical impulse.

As may be recognized by those skilled in the pertinent art based on the teachings herein, the face of the reflective layer 118 may be specially configured for directing a high percentage of the incident photons directly towards the phototransistors 123, such as, for example, by having a slightly convex shape, one or more aspheric or condensing lenses, a laser splitter mounted thereon, and/or like features for better directing the reflected light towards the phototransistors. An electronic circuit 124 is mounted to the housing 120. The electronic circuit 124 receives the outputs from the phototransistors 123, and generates signals indicative of the movement of the diaphragm 114. A speaker 126 is mounted to the housing and produces audible outputs corresponding to the signals generated and amplified by the circuit 124, and indicative of the movement of the diaphragm 114. The sensor assembly 112 further comprises an acoustic diaphragm 138 mounted to the housing 120 at the end opposite that of the diaphragm 114. A selection manifold 136 is also mounted to the housing 120, and may be acoustically coupled to either the acoustic diaphragm 138 or the speaker 126 by rotating the manifold 180 degrees relative to the housing 120.

Turning now to FIG. 7, the electronic circuit 124 is illustrated in further detail. The phototransistors 123 are connected in parallel, emitters to emitters and collectors to collectors, so that the reception of laser light at any one or more of their respective gates will generate a signal to excite the circuit. The collectors are connected to a resistor 181, which, in turn, is connected to the positive voltage potential ("$V_{BAT}$") terminal of a battery 132. The negative terminal of the battery 132 is connected to ground potential. The collectors are also connected to a capacitor 182, which is then connected to a resistor 183. The resistor 183 is connected to an inverting input of an op-amp 184. An output of the op-amp 184 is connected to a feedback resistor 185, which is then connected back to the inverting input of the op-amp. The non-inverting input of the op-amp 184 is connected to a voltage drop resistor 186, which is connected in turn to $V_{BAT}$. The non-inverting input of the op-amp is also connected to a parallel combination of a capacitor 187 and a resistor 188, which are then connected to ground potential. The op-amp 184 functions as an amplifier for the signal generated by the phototransistors 123, which, in turn, is indicative of a cardiac motion or impulse. The output of the op-amp 184 is further connected to a capacitor 189. The capacitor 189 is connected, in turn, to a potentiometer 190. The fixed output of the potentiometer 190 is connected through a capacitor 191 to $V_{BAT}$. The fixed output terminal of the potentiometer 190 is further connected to an inverting input of a comparator 192. The variable output terminal of the potentiometer 190 is connected to a resistor 193, which is then connected to a non-inverting input of the comparator 192. The adjustment of the potentiometer 190 affects the duration of the pulse generated by the comparator 192. The output of the comparator 192 is connected to a capacitor 194, which is ultimately connected to a first terminal of the speaker 126. A second terminal of the speaker 126 is connected to ground potential. Thus, the speaker 126 is activated for each rise in amplitude of a cardiac apical impulse waveform detected by the phototransistors 123.

In operation, the sensor assembly 112 of the cardiac impulse detector 110 is placed on the cardiac apical impulse of a patient, with the resilient layer 116 contacting the patient's chest surface at the cardiac apical impulse. A cardiac apical impulse induces motion of the resilient layer 116, which in turn causes motion of the diaphragm 114 and the reflective layer 118. The laser diode 117 emits laser light towards the reflective layer 118. The light is reflected by the reflective layer 118, and received by the phototransistors 123. The circuit 124 incorporates the phototransistors in an electronic motion detection scheme as described above, and drives the speaker 126 corresponding to motions of the resilient layer 116, which is hence keenly indicative of the cardiac apical motion.

The cardiac impulse detector 110 is capable of detecting and audibly representing the infrasonic vibrations of the cardiac apical impulse. There are three repetitive major vibrations detected by this device during a regular heart rhythm.

The first of these vibrations occurs at the beginning of the left ventricular ("LV") recoil and causes the detector 110 to produce a first audible signal through the speaker 126 representing the beginning of LV recoil. The second of these vibrations occurs at the beginning of LV ejection and causes the detector 110 to produce a second audible signal through the speaker 126 representing the beginning of LV ejection, and the third of these vibrations occurs at the beginning of LV filling and causes the detector 110 to produce a third audible signal through the speaker 126 representing the beginning of LV filling. The first audible signal occurs in close timing to the normal first heart sound and the counted pulse, and the second audible signal occurs in close timing to the normal second heart sound. The third audible signal occurs after the second heart sound. These three audible signals represent directional change of the cardiac apical impulse motion.

These three audible signals are easily recognized and learned by a caregiver. Additional audible signals, which represent abnormal vibrations that are detected during ventricular filling, would thus represent gallops and indicate cardiac pathology.

S3 and S4 types of gallops are detectable using the cardiac impulse detector 110. An extra vibration detected and audibly indicated by the speaker 126, preceding the first vibration, represents an S4 gallop. An extra vibration detected and audibly indicated by the speaker 126 soon after the third vibration represents an S3 gallop. As may be recognized by those skilled in the pertinent art based on the teachings herein, these detected vibrations and associated output signals could also be indicated visually by means of an LED, and/or displayed graphically using analog or digital processing electronically interfaced to a charge-coupled device or LCD screen. The analog or digital processing also affords electronic storage, playback, compression and analysis of output signals indicative of normal and abnormal vibrations of the cardiac apical impulse.

As may also be recognized by those skilled in the pertinent art based on the teachings herein, numerous different processing circuits may be added or substituted for the electronic circuit 124 disclosed herein, in order to produce various signals indicative of particular types of gallops and other abnormal cardiac apical impulses. In addition, as may be recognized by those skilled in the pertinent art based on the teachings herein, when signals indicative of both the infrasonic impulses and the acoustic heart sounds are made present in electronic form, the electronic circuit may utilize the signals indicative of acoustic sounds to supplement the qualification, analysis, and/or categorization of gallops and other abnormal cardiac apical impulses.

Figure 8:
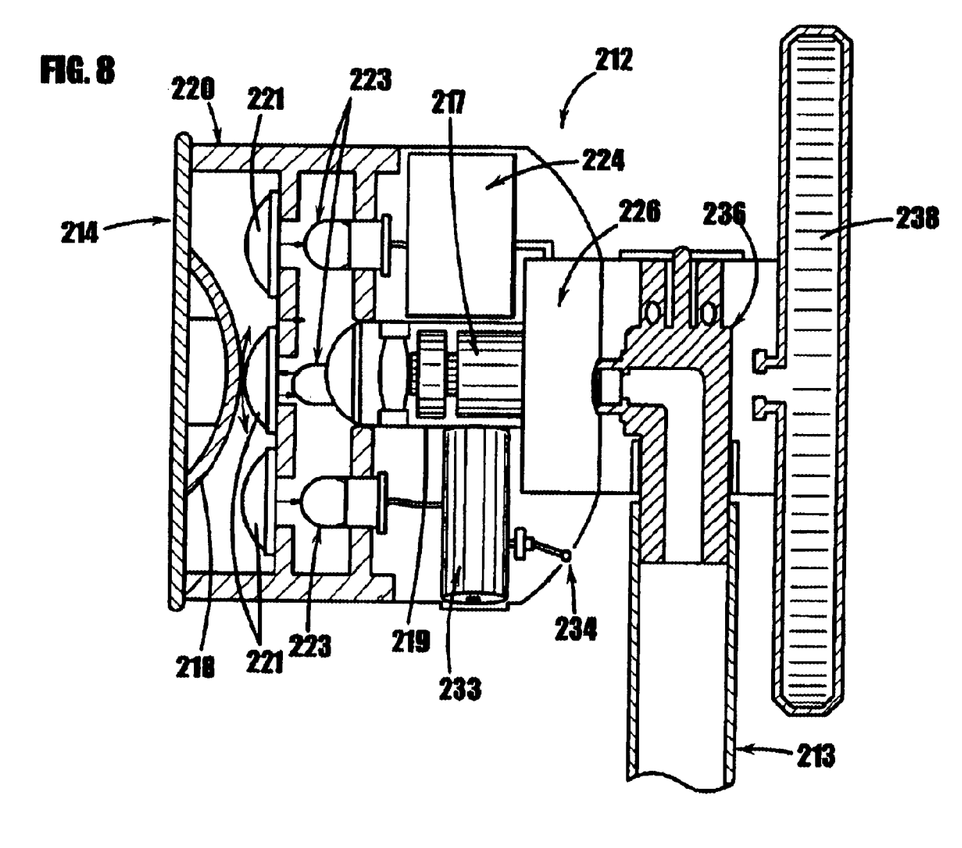
FIG. 8 is a cross-sectional view of a third embodiment of a cardiac impulse detector embodying the present invention.

In FIG. 8, a third embodiment of the cardiac impulse detector sensor assembly of the present invention is indicated generally by the reference numeral 212. The cardiac impulse detector sensor assembly 212 is substantially similar to the cardiac impulse detector sensor assembly 112 described above, and therefore like reference numerals preceded by the numeral 2 are used to indicate like elements. The cardiac impulse detector sensor assembly 212 of FIG. 8 differs from that of FIG. 6 primarily in that the sensor assembly 212 utilizes a convex reflector and convex collecting lenses with a compatible sensing scheme in lieu of the laser reflector of FIG. 6. The application and overall operation of the cardiac impulse detector sensor assembly 212 is substantially similar to that of the cardiac impulse detector sensor assembly 112.

As shown in FIG. 8, the cardiac impulse detector sensor assembly 212 comprises a flexible diaphragm 214 mounted about its circumference to a housing 220. An electrical power switch 234 is mounted to the housing 220 for activating the cardiac impulse detector. An audio amplifier 215 is connected to the tubing 213, and is electrically connected to the power switch 234, for enhancing the quality of the audio signal.

The diaphragm 214 is connected on its inside surface to a convex reflective structure 218. In this embodiment of the present invention, the reflective structure 218 is coated on its outer surface with any reflective material, such as that sold under the trademark REFLEXITE®. As may be recognized by those skilled in the pertinent art based on the teachings herein, the reflective structure 218 may comprise various other materials having comparably high coefficients of reflectivity, which are currently or later become known for performing the functions of the exemplary reflective surface of the structure. A laser diode support 219 is mounted to an inner surface of the housing 220, and projects outwardly towards the diaphragm 214. A laser diode 217 is mounted to the free end of the support 219, and emits a beam of laser light towards the center of the reflective structure 218. A battery 233 is mounted to the housing 220, and is electrically connected to the laser diode 217 via a power switch 234 for supplying power to the diode. Condensing lenses 221 are mounted to an inner wall of the housing 220, and are optically coupled to phototransistors 223, which are mounted to the laser support 219. The phototransistors 223 receive the reflected laser light through the condensing lenses 221 that is directed by the reflective structure 218, and generate outputs indicative of the instantaneous position of the diaphragm 214 that are proportional to the infrasonic movements of the cardiac apical impulse.

An electronic circuit 224 is mounted to the housing 220. The electronic circuit 224 receives the outputs from the phototransistors 223, and generates signals indicative of the movement of the diaphragm 214. The electronic circuit 224 is substantially similar to the electronic circuit 124, described above.

In operation, the sensor assembly 212 of the cardiac impulse detector 210 is placed on the cardiac apical impulse of a patient, with the flexible diaphragm 214 contacting the patient's chest surface at the cardiac apical impulse. A cardiac apical impulse induces motion of the diaphragm 214 and the reflective structure 218. The laser diode 217 emits laser light towards the reflective structure 218. The light is reflected by the reflective structure 218, condensed by the condensing lenses 221, and received by the phototransistors 223. The circuit 224 incorporates the phototransistors in an electronic motion detection scheme as described above, and drives the speaker 226 corresponding to motions of the flexible diaphragm 214, which is keenly indicative of the cardiac apical motion.

The cardiac impulse detector 210 detects and audibly represents the infrasonic vibrations of the cardiac apical impulse. There are three representative major signals detected by this device during a regular heart rhythm. The first audible signal produced by the detector through the speaker 226 represents the beginning of left ventricular recoil, the second audible signal produced by the detector represents the beginning of left ventricular ejection, and the third audible signal produced represents the beginning of left ventricular filling. These three audible signals are easily learned by a caregiver. Additional sounds produced by the detector, which represent abnormal vibrations detected during ventricular filling, would thus represent gallops and indicate cardiac pathology. As may be recognized by those skilled in the pertinent art based on the teachings herein, these signals may be displayed graphically as well as audibly, such as, for example, by using analog or digital processing, a charge coupled device and a LCD output screen. This embodiment also offers the advantages of electronic storage, playback, compression and analysis of normal and abnormal signals.

The cardiac impulse detector 210 further detects S3 and S4 gallops. When a patient presents with an S3 gallop, the speaker 226 will produce a sound immediately following the third sound. When a patient presents with an S4 gallop, the speaker 226 will produce a sound immediately preceding the first sound.

As may be recognized by those skilled in the pertinent art based on the teachings herein, numerous different processing circuits may be added or substituted for the electronic circuit 224 disclosed herein, in order to produce various signals indicative of particular types of gallops and other abnormal cardiac apical impulses. In addition, as may be recognized by those skilled in the pertinent art based on the teachings herein, when signals indicative of both the infrasonic impulses and the acoustic heart sounds are made present in electronic form, the electronic circuit may utilize the signals indicative of acoustic sounds to supplement the qualification, analysis, and/or categorization of gallops and other abnormal cardiac apical impulses.

One advantage of the above-described embodiments of the present invention is that an audible signal indicative of an infrasonic cardiac apical impulse may be generated for contemporaneous diagnosis by a medical caregiver.

Another advantage of the above-described embodiments of the present invention is that an audible signal indicative of an S3 or S4 gallop may be generated during a brief physical examination of a patient.

A further advantage of the above-described embodiments of the present invention is that an audible signal indicative of an infrasonic cardiac apical impulse may be supplied in context with traditional acoustic cardiac sounds to promote efficient examination and diagnosis of a patient.

An additional advantage of the above-described embodiments of the present invention is that an audible signal indicative of an infrasonic cardiac apical impulse may be generated in a medical school curriculum to promote enhanced understanding of the clinical manifestations of various heart diseases.

As may be recognized by those skilled in the pertinent art based on the teachings herein, numerous changes may be made to the above described and other embodiments of the present invention without departing from its scope or spirit as defined in the appended claims. For example, alternate or supplemental sensors capable of sensing the low frequency vibrations or impulses generated by the heart include piezoelectric crystals, piezoelectric films, accelerometers, silicon pressure transducers, lasers, and other displacement devices. These low frequency vibrations also can be detected by electromagnetic field devices such as inductance transducers. Therefore, any of a number of sensing devices presently available or later developed may be used to augment or replace the sensors used for exemplary purposes herein.

Similarly, the particular hardware used for the acoustic diaphragm may be electronically augmented, and the earpiece, tubing, and housing may be replaced with hardware having similar functionality without departing from the scope and spirit of the present invention.

Likewise, the acoustic diaphragm itself may be replaced with a microphone, piezoelectric audio sensor, or similar mechanism, such that the processing of the infrasonic and audible cardiac motions may be done electronically to produce an audible output for the first time at one or more earpiece transducers.

In addition, a single sensor may be used to sense both infrasonic motions and audible sounds. For example, a piezoelectric sensing diaphragm may be used to sense both infrasonic motions and audible sounds when combined with a sensing protuberance capable of transmitting infrasonic motions and audible frequencies such that the audible sounds are not damped out by the mechanical loading of the sensing protuberance against the tissue of a patient.

Accordingly, this Detailed Description of the Preferred Embodiments is to be taken in an illustrative as opposed to a limiting sense.

What is claimed is:

1. An apparatus for detecting infrasonic cardiac apical impulses of a patient, comprising:

a flexible substrate including (i) a flexible skin-contacting surface located on one side of the substrate that is disposable in contact with a skin surface region of a patient defining an infrasonic cardiac apical impulse point, and is movable with the contacted skin surface region in response to a subaudible motion of the contacted skin at the infrasonic cardiac apical impulse point, and (ii) a flexible reflective surface located on an opposite side of the substrate relative to the skin-contacting surface and movable with the skin-contacting surface in response to a subaudible motion of the contacted skin at the infrasonic cardiac apical impulse point;

a light source spaced apart from and facing the reflective surface of the substrate that transmits light onto the reflective surface, and wherein the reflective surface reflects light transmitted thereon by the light source;

an optical sensor spaced apart from and facing the reflective surface that receives reflected light directed by the reflective surface and generates a first signal indicative of movement of the reflective and skin-contacting surfaces and corresponding to a subaudible motion of the contacted skin at the infrasonic cardiac apical impulse point; and a first circuit coupled to the optical sensor for generating at least one of (i) an audible output and (ii) a visual output, in response to the first signal and indicative of an infrasonic cardiac apical impulse.

2. An apparatus as defined in claim 1, wherein the optical sensor comprises:

at least one phototransistor or photodiode optically coupled to the reflective surface.

3. An apparatus as defined in claim 1, wherein the first circuit comprises:

circuitry for generating at least one optical output in response to the first signal and indicative of the infrasonic cardiac apical impulse.

4. An apparatus as defined in claim 1, further comprising:

a second sensor disposable in contact with the skin of the patient for producing a signal responsive to an audible cardiac sound of the patient.

5. An apparatus as defined in claim 4, further comprising:

a sensor housing, wherein:
the flexible substrate is mounted at one end of the housing;
the second sensor is located at an end of the housing opposite to that of the flexible substrate;
the second sensor is an acoustic diaphragm having an acoustic output; and
the apparatus further comprises an earpiece coupled to the optical and second sensors for receiving the at least one audible and acoustic outputs.

6. An apparatus as defined in claim 5, further comprising:

a selection manifold coupled to the earpiece for selectable transmission of the the outputs to the earpiece.

7. An apparatus as defined in claim 6, further comprising:

an electronic amplifier having an enhanced audible output, coupled between the selection manifold and the earpiece.

8. An apparatus as defined in claim 1, wherein the at least one output is indicative of S3 and S4 gallops.

9. An apparatus as defined in claim 1, further comprising a housing, and wherein the flexible substrate is mounted within the housing.

10. An apparatus as defined in claim 9, wherein the light source, optical sensor, and first circuit are mounted within the housing.

11. An apparatus as defined in claim 1, wherein the flexible substrate includes a resilient layer forming the skin-contacting surface, and a reflective layer superimposed over the resilient layer and forming the reflective surface.

12. An apparatus as defined in claim 1, wherein the light source is a laser.

13. An apparatus as defined in claim 1, further comprising at least one of a liquid crystal display, graphical monitor and computational device, coupled to the first circuit for generating a visual output.

14. An apparatus as defined in claim 1, wherein the flexible substrate is in the form of a diaphragm, and the reflective surface extends throughout at least a central region of the diaphragm.

15. A method for detecting infrasonic cardiac apical impulses of a patient, comprising the following steps:

providing a flexible substrate including a flexible skin-contacting surface located on one side of the substrate and a flexible reflective surface located on an opposite side of the flexible substrate relative to the skin-contacting surface;

positioning the skin-contacting surface of the flexible substrate in contact with a skin surface region of the patient defining an infrasonic cardiac apical impulse point on the patient's chest;

allowing movement of the skin-contacting and reflective surfaces of the flexible substrate with movement of the skin surface region of the patient in response to a subaudible motion of the skin at the infrasonic cardiac apical impulse point;

transmitting light from a light source onto the reflective surface of the flexible substrate positioned on the skin surface region of the patient defining the infrasonic cardiac apical impulse point;

reflecting transmitted light from the light source with the reflective surface of the flexible substrate positioned on the skin surface region of the patient defining the infrasonic cardiac apical impulse point;

receiving with an optical sensor reflected light directed by the reflective surface and generating a first signal indicative of movement of the reflective and skin-contacting surfaces and corresponding to a subaudible motion of the skin at the infrasonic cardiac apical impulse point;

processing the first signal electronically; and generating at least one of (i) an audible output, and (ii) a visual output, indicative of an infrasonic cardiac apical impulse.

16. A method as defined in claim 15, wherein:

the step of processing comprises electronically processing the first signal to determine the presence of S3 and S4 gallops; and the step of generating comprises generating a first output indicative of the S3 and S4 gallops.

17. A method as defined in claim 15, further comprising the following steps:

sensing an audible cardiac sound of the patient; and
generating an audible output indicative of the audible cardiac sound.

18. A method as defined in claim 15, further comprising the steps of providing a flexible substrate in the form of a diaphragm, and positioning the diaphragm in conformable contact with the infrasonic cardiac apical impulse point on the patient's chest and a skin region surrounding said point.

19. An apparatus for detecting infrasonic cardiac apical impulses of a patient, comprising:

first means for flexibly contacting a skin surface region of a patient defining an infrasonic cardiac apical impulse point and for moving with the contacted skin surface region in response to a subaudible motion of the contacted skin at the infrasonic cardiac apical impulse point;

second means located on a side of the first means opposite the contacted skin surface region of the patient for flexibly moving with the first means in response to a subaudible motion of the contacted skin at the infrasonic cardiac apical impulse point and for reflecting light transmitted thereon;

third means for transmitting light onto the second means;

fourth means for receiving reflected light from the second means and for generating a first signal indicative of movement of the first and second means and corresponding to a subaudible motion of the contacted skin at the infrasonic cardiac apical impulse point; and fifth means coupled to the fourth means for generating at least one of (i) an audible signal, and (ii) a visual signal, in response to the first signal and indicative of the infrasonic cardiac apical impulse.

20. An apparatus as defined in claim 19, wherein:

the first signal generated by the fourth means is responsive to cardiac apical impulses exhibiting at least one of S3 and S4 gallops; and the signal generated by the fifth means is indicative of S3 and S4 gallops.

21. An apparatus as defined in claim 19, further comprising:

sixth means for sensing an audible cardiac sound of the patient; and seventh means coupled to the sixth means for generating an audible signal in response to the sixth means and indicative of the audible cardiac sound.

22. An apparatus as defined in claim 21, wherein:

the sixth means is an input side of an acoustic diaphragm; and the seventh means is an output side of the acoustic diaphragm.

23. An apparatus as defined in claim 21, further comprising:

eighth means coupled to the fourth and seventh means for selectably transmitting a signal indicative of at least one of the cardiac events sensed by the second and sixth means.

24. An apparatus as defined in claim 21, further comprising:

ninth means coupled to the seventh means for audibly enhancing the signal generated by the seventh means, and generating an enhanced audible signal corresponding thereto.

25. An apparatus as defined in claim 24, wherein:

the first signal generated by the fourth means is responsive to cardiac apical impulses exhibiting S3 and S4 gallops;

the audible signal generated by the fifth means is indicative of S3 and S4 gallops;

the audible signal generated by the seventh means is indicative of a difference between S3 and S4 gallops; and the ninth means is coupled to the fifth and seventh means for audibly enhancing the signals generated by the fifth and seventh means, and the enhanced audible signal generated by the ninth means is indicative of one or the other S3 and S4 gallops.

26. An apparatus as defined in claim 19, wherein the first means is a skin-contacting surface of a flexible substrate.

27. An apparatus as defined in claim 19, wherein the second means is a reflective surface of a flexible substrate.

28. An apparatus as defined in claim 19, wherein the third means is a laser.

29. An apparatus as defined in claim 19, wherein the fourth means is an optical sensor.

* * * * *